United States Patent [19]
Kuhry

[11] Patent Number: 5,186,171
[45] Date of Patent: Feb. 16, 1993

[54] ELECTROTHERAPY DEVICE AND PROCESS

[76] Inventor: Anthony B. Kuhry, 6209 N. Mozart St., Chicago, Ill. 60659

[21] Appl. No.: 657,659

[22] Filed: Feb. 19, 1991

[51] Int. Cl.⁵ .............................................. A61N 1/06
[52] U.S. Cl. .................................. 128/421; 128/783; 128/798
[58] Field of Search ................... 128/421, 419 R, 783, 128/798, 422

[56] References Cited

U.S. PATENT DOCUMENTS

| | | | |
|---|---|---|---|
| 3,670,737 | 6/1972 | Pearo | 128/422 |
| 4,197,851 | 4/1980 | Fellus | 128/798 |
| 4,667,677 | 5/1987 | Di Mino | 128/419 R |
| 4,932,420 | 6/1990 | Goldstein | 128/783 |

*Primary Examiner*—Kyle L. Howell
*Assistant Examiner*—Scott M. Getzow
*Attorney, Agent, or Firm*—Lee, Mann, Smith, McWilliams, Sweeney & Ohlson

[57] ABSTRACT

An electrotherapy device and process for treatment of musculoskeletal disorders. The device comprises an antenna formed of a series of spaced conductive strips, a high voltage, high frequency, low power source connected to the antenna, and dielectric shielding for preventing arcing from the device during treatment of a disorder. In the treatment process, a high voltage, high frequency, pulsed source is provided to produce a broad band output corona discharge from the antenna having an electrostatic field extending in frequency from 0 Hz to over 1 GHz and constantly changing randomly in amplitude and frequency. The excited antenna is applied to a body with the corona discharge enveloping a region experiencing a musculoskeletal disorder.

20 Claims, 5 Drawing Sheets

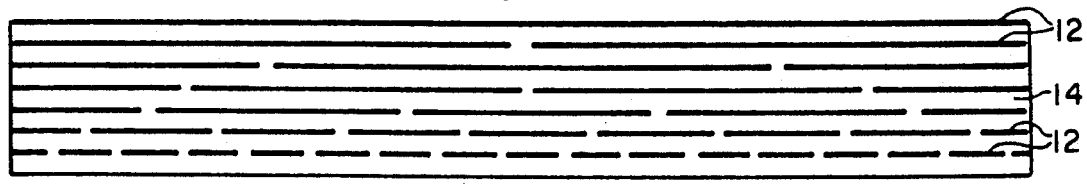
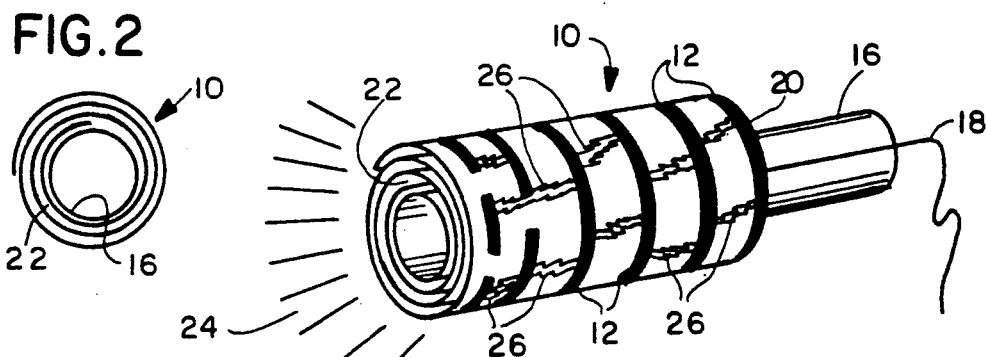
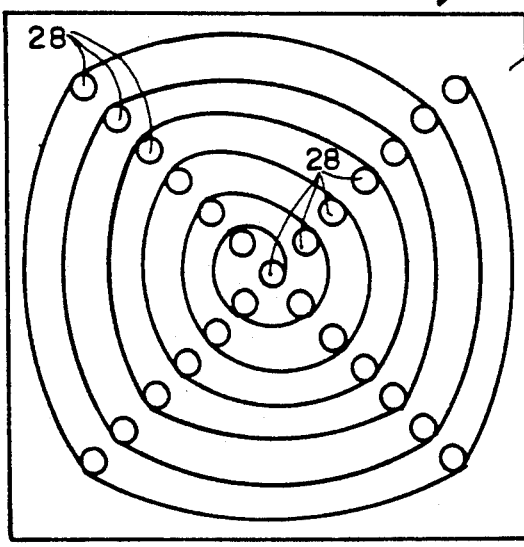
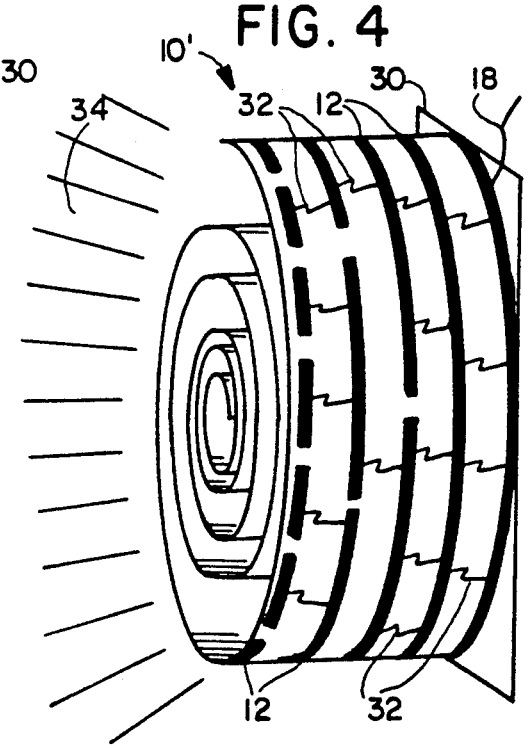

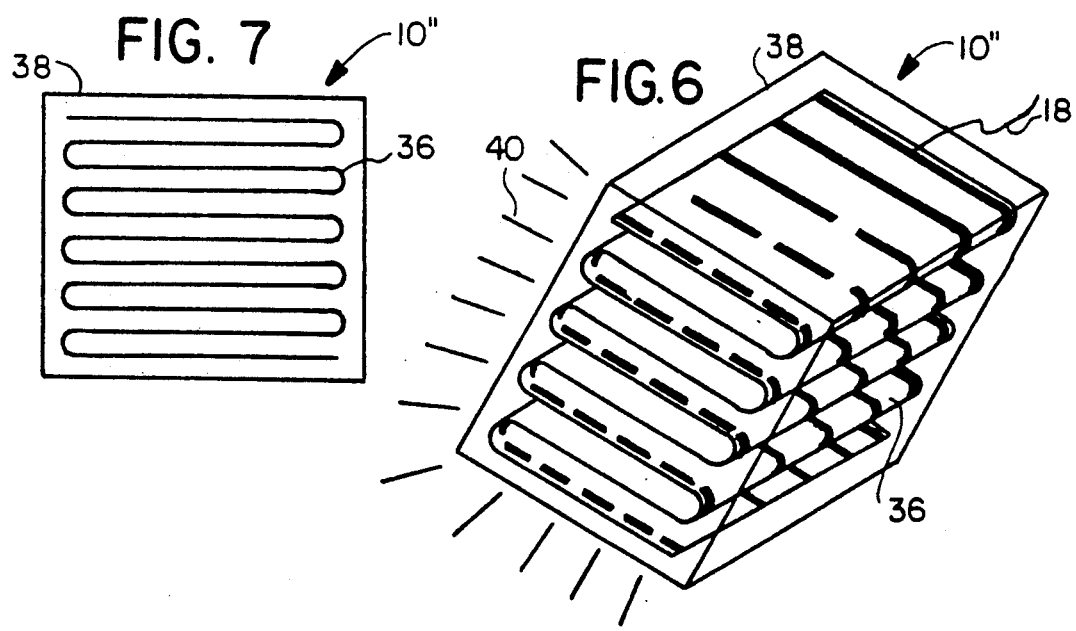
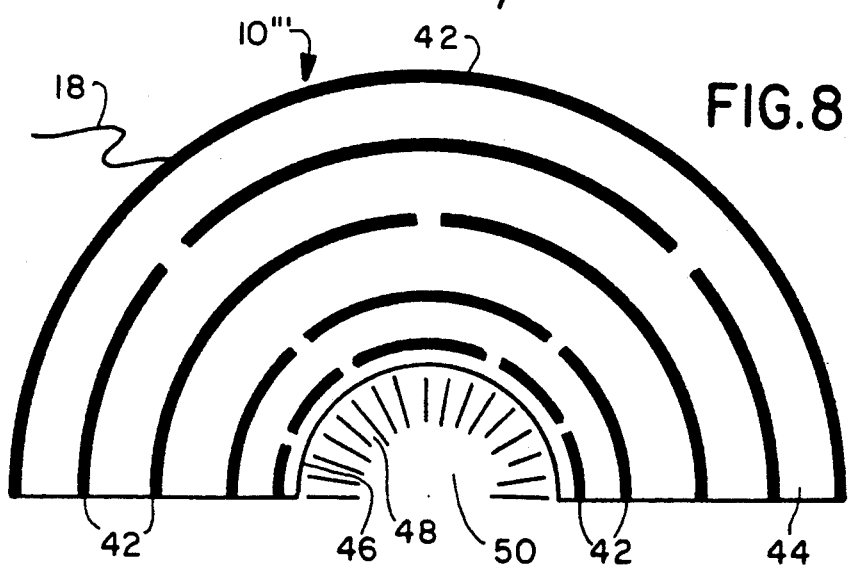
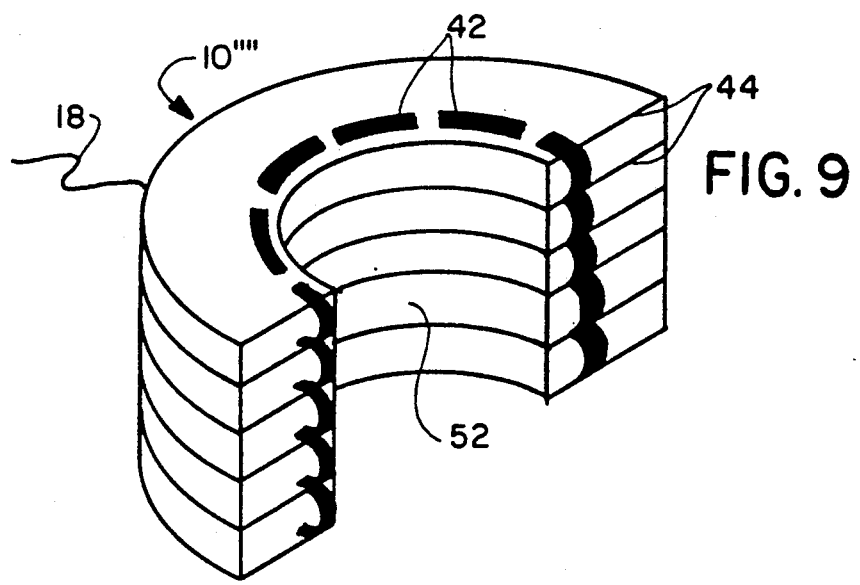

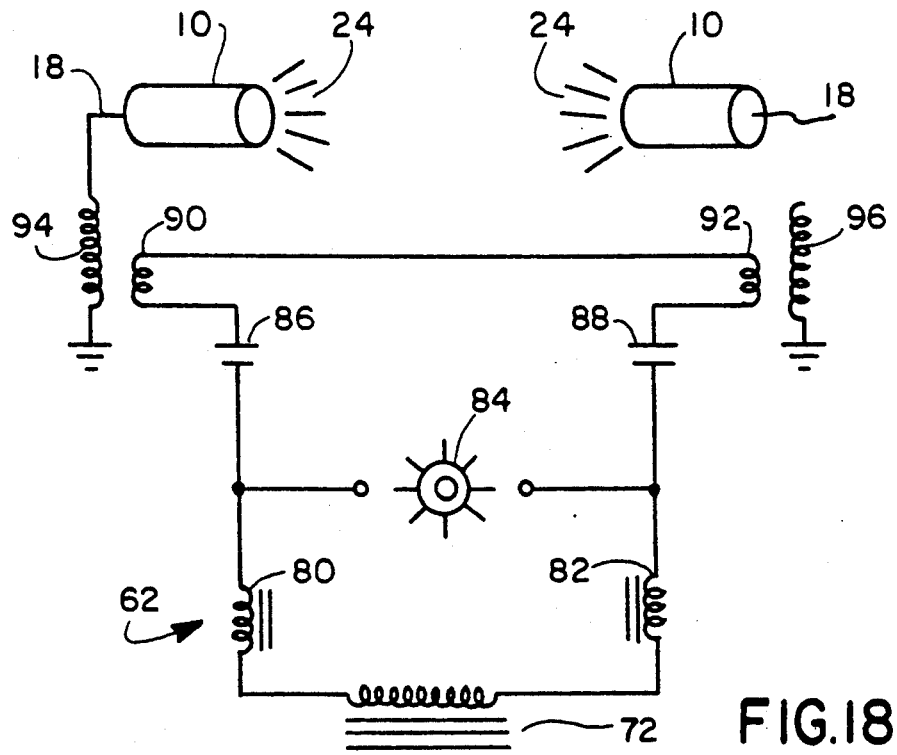
FIG.18
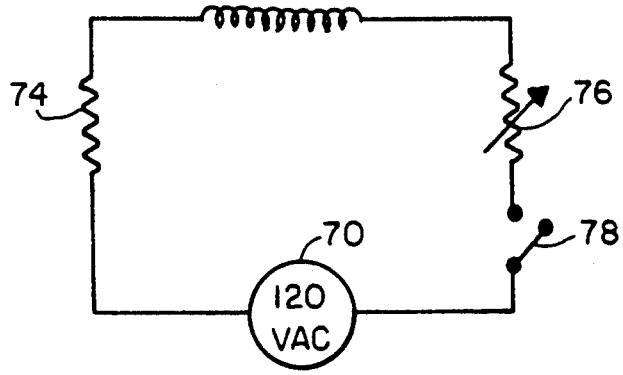
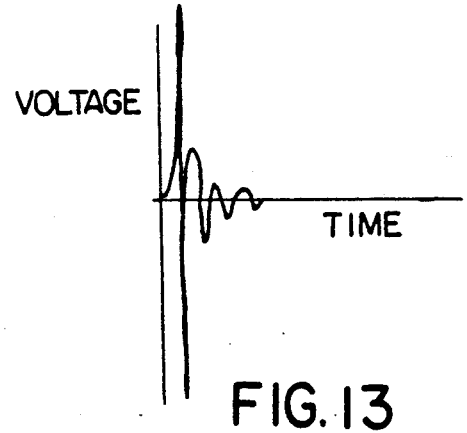
FIG.13
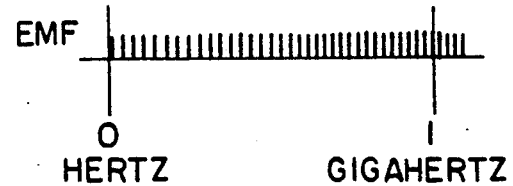
FIG.14

ELECTROTHERAPY DEVICE AND PROCESS

BACKGROUND OF THE INVENTION

This invention relates to electrotherapy devices, and in particular to an electrotherapy device and process for treatment of musculoskeletal disorders by applying a broad band high frequency, low power, high voltage corona to the body being treated.

Corona discharge therapy techniques are known. For example, U.S. Pat. No. 4,667,677, the disclosure of which is incorporated herein by reference, relates to a device and process for thermal therapy relief of arthritic and other body pain. By generating heat energy induced into an area of pain, a salutary effect of reduction of pain is ultimately experienced.

One effect of such systems is the generation of heat energy in an area of pain. That is an undesirable effect, and limits the time that therapy can be applied to the patient before undue heating occurs, or pain or injury results.

Another therapeutic device is disclosed in U.S. Pat. No. 3,670,737, relating to the "Diapulse" system. However, this system also generates heat in the treated area, and suffers the same disadvantages as U.S. Pat. No. 4,667,677.

SUMMARY OF THE INVENTION

The present invention relates to an electrotherapy device and process for treatment of musculoskeletal disorders. The device comprises an antenna having a high voltage application location and a corona discharge location, with the two locations being spaced from one another. The antenna is formed of a plurality of spaced rows of conductive strips which extend transversely between the application and discharge locations, each row having at least one strip with the number of strips in each row increasing generally from the application location to the discharge location while the lengths of the strips simultaneously decreases. The strips are appropriately mounted so that they are out of contact with one another. A high voltage, high frequency, low power source is connected to the application location, and dielectric shielding is provided at the discharge location for preventing arcing from the electrotherapy device during treatment of a disorder.

In accordance with the preferred form of the invention, the conductive strips are mounted on a dielectric plastic sheet, with the strips being adhesively secured or otherwise affixed to the sheet. In one form of the invention, the strips are secured to the sheet in parallel rows, and the sheet is wound into a tight spiral coil with the application and discharge locations being situated at opposite ends of the coil. In this form of the invention, dielectric shielding may encase the coil, or may simply be a sheet of dielectric material situated at the discharge location.

In another form of the invention, instead of a tightly wound coil, the sheet is wound into spaced, spiral convolutions. To separate the convolutions, a series of pegs is provided spacing each convolution from the next. Again, dielectric shielding is also used.

In yet another form of the invention, the conductive strips are secured to the sheet in parallel rows, and the sheet is then accordion folded into a stack with the discharge and application locations being on opposite sides of the stack. The stack can be tightly folded, or loosely folded in a fashion similar to the spaced spiral convolutions.

In accordance with another form of the invention, the conductive strips are secured to the sheet in curved, radially spaced rows, with the discharge location being located at a treatment area at least partially enveloped by an inner row of the rows of conductive strips. In this form of the invention, a single flat sheet can be formed, or a series of stacked and aligned sheets may form an appropriate treatment device.

In yet another form of the invention, a pair of the antennas is used for treatment, spaced from one another with a treatment area being located between the antennas. The antennas may be permanently encased in a unit, or may be temporarily situated to provide a treatment area therebetween.

In all forms of the invention, the dielectric shielding is utilized, and is composed of a low loss dielectric plastic which operates as an insulator to prevent arcing from the antenna to the patient being treated.

In treatment of a disorder, after the antenna has been formed, a high voltage, high frequency source is generated, and is pulsed at a low frequency rate to produce a broad band output corona discharge from the discharge location of the antenna. The output has an electrostatic field extending in frequency from 0 Hz to over 1 GHz and is constantly changing randomly in amplitude and frequency. The corona is applied directly to the surface of a body in a region experiencing a musculoskeletal disorder, without invading the tissue for treatment.

The voltage of the power source for the device is preferably in the range of from about 100,000 to about 200,000 volts, with 150,000 volts being preferred. The frequency of the device is about ½ MHz. The low frequency pulse rate of the device is about 120 Hz, and the power source has a power output of from 5 to 15 watts.

BRIEF DESCRIPTION OF THE DRAWINGS

The invention is described in greater detail in the following description of examples embodying the best mode of the invention, taken in conjunction with the drawing figures, in which:

FIG. 1 is an illustration of the formation of one antenna according to the invention, showing spaced conductive strips on a plastic sheet, FIG. 2 is an end view of a tightly wound antenna, wound from the sheet of FIG. 1, FIG. 3 is a perspective view thereof, schematically showing spark discharges between adjacent conductive strips and illustrating the corona discharge, FIG. 4 is a perspective view of a second form of the invention, in which the plastic sheet of FIG. 1 is loosely wound into spaced, spiral convolutions, FIG. 5 is an end view of the form of the invention shown in FIG. 4, FIG. 6 is another form of the invention, in which the sheet of FIG. 1 is accordion folded into a stack, FIG. 7 is an end view thereof, FIG. 8 illustrates yet another form of the invention, in which the conductive strips are placed in an arcuate form on a similarly-shaped sheet, FIG. 9 is a perspective view of a stacked series of the sheets of FIG. 8, FIG. 10 diagrammatically illustrates utilization of two of the antennas of FIGS. 2 and 3 to provide a treatment area therebetween, FIG. 11 diagrammatically illustrates a single antenna such as that of FIG. 3, and having a handle for portability and ease of utility, FIG. 13 illustrates the high voltage output wave form applied to the antennas of FIGS. 1-12, FIG. 14 illustrates the output of the antennas of FIGS. 1-12, showing a broad band, random yet consistent output from 0 Hz to over 1 GHz, FIG. 18 is a schematic circuit illustration for operating a pair of the antennas according to the invention.

DESCRIPTION OF EXAMPLES EMBODYING THE BEST MODE OF THE INVENTION

Figure 10:
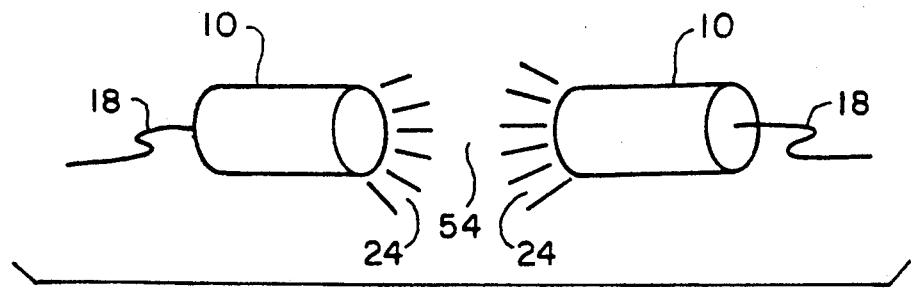

For the treatment antenna, the invention employs a high voltage discharge antenna composed of a series of thin, individual conductive strips which do not contact one another and which are separated from one another on a dielectric plastic sheet formed appropriately to constitute the antenna. The antenna is excited from one end by a pulsed, high frequency, high voltage source which delivers between 100,000 and 200,000 volts at a power of between 5 to 15 watts, thus resulting in very low currents. The frequency of the source is about ½ MHz, and is pulsed at a frequency of about 120 Hz. However the antenna is formed, the output of the antenna is shielding by a low loss dielectric plastic shield that insulates the body being treated from high voltage arcs.

Various forms of antennas according to the invention are shown at 10, 10', etc. in the drawing figures. It will be evident that other antenna forms can be utilized, as well, so long as the basic features of the invention are followed.

The antennas of FIGS. 1-7 are formed of a plurality of conductive strips 12, such as copper, aluminum, etc., applied to a dielectric plastic sheet 14. The sheet shown in FIG. 1 is about 4 feet in length, and about 4 inches in width. The strips 12, as illustrated, extend in spaced rows, with each row having at least one strip and with the numbers of strips in each row increasing generally from one edge of the sheet 14 to the other (and the lengths of the strips decreasing), until, as illustrated, a relatively large number of small strips are located in the final row which, when the antenna is formed, is adjacent the corona discharge location or end of the antenna. The strips 12 are adhesively or otherwise applied to the sheet 14 so that the strips are permanently affixed without contacting one another.

Shown in FIGS. 2 and 3 is a first form of antenna 10 according to the invention. The antenna 10 is formed by tightly winding the sheet 14 about a hollow plastic tube 16. A conductor 18 leads from the antenna 10 and is connected to a high voltage, high frequency source, described below in connection with FIGS. 18 and 19.

The antenna 10 includes a voltage application end or location 20 to which the conductor 18 is attached, and a corona discharge end or location 22, from which a corona 24 is emitted when the antenna 10 is excited. When the antenna 10 is excited, high voltage electrical discharges 26 occur between the adjacent strips 12, producing a corona discharge throughout the interior of the device 10, and being emitted as shown at 24.

In this form of the invention, and indeed in all forms of the invention, a dielectric shield is utilized at the discharge end 22 to protect the patient. Various shields are discussed below in connection with FIGS. 15-17.

FIGS. 4 and 5 illustrate a second form of antenna 10' according to the invention, formed from the same sheet 14 illustrated in FIG. 1. In this form of the invention, the sheet 14 is coiled into spaced, spiral convolutions separated by a series of pegs 28 secured to a plastic mounting plate 30. As in the first form of the antenna shown in FIGS. 2 and 3, the antenna 10' is excited by application of a high voltage, high frequency source, resulting in high voltage discharges 32 between adjacent strips 12 of the sheet 14. This causes a corona discharge 34 from the antenna 10'.

A third form of an antenna 10'' according to the invention is illustrated in FIGS. 6 and 7. In this form of the invention, again the antenna 10'' is formed from the sheet 14 illustrated in FIG. 1, which has been accordion folded into a stack 36. The stack 36 may be held in place and encased within a dielectric plastic encasement 38, or may otherwise be held in place. Adjacent folds of the stack 36 may be separated by pegs, in the fashion shown in FIG. 5, may be folded directly upon one another, or may be otherwise spaced by other dielectric material. In a fashion similar to that of the forms of the invention of FIGS. 2-4, excitation of the stack 36 from a remote power source creates a corona 40 from a discharge end or location opposite to that to which the exciting voltage is applied through the conductor 18.

In the forms of the invention illustrated in FIGS. 1-7, the strips 12 are formed in parallel rows on the sheet 14. A further form of antenna 10''' is shown in FIG. 8, this form of the invention having a series of curved strips 42 which are secured to a dielectric sheet 44 in radially spaced rows. The outermost strip 42 is the longest strip, and is connected by a conductor 18 to a source of high voltage, high frequency power. The length of the strips 42 decrease radially inwardly from the outermost strip, to an inner corona discharge location 46 from which a corona 48 is emitted into a treatment area 50. The form of the invention shown in FIG. 8 is particularly useful for treating arms, legs and other body parts that can be situated in the treatment area 50.

A series of the sheets 44 is stacked to form yet another antenna 10'''' as shown in FIG. 9. In this form of the invention, most of the strips 42 have been omitted for purposes of illustration. Also, in this form of the invention the strips 42 of each row of each sheet 44 are shown as interconnected, although not required. The stacked sheets 44 of the antenna 10'''' form a treatment area 52 in the inner U-shaped cavity of the antenna 10''''.

FIG. 10 illustrates use of pair of antennas 10, emitting their coronas 24 toward one another and forming a treatment area 54 therebetween. The two antennas 10 are connected by their respective conductors 18 to a high voltage, high frequency source, such as that illustrated in FIG. 18 and described below.

Figure 11:
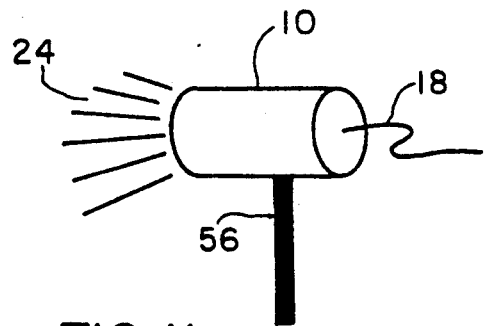

For reaching hard to treat areas, the antenna 10 may be mounted on a handle 56, as shown in FIG. 11. This portable form of the invention is therefore quite versatile, limited in range only by the length of the conductor 18.

Figure 12:
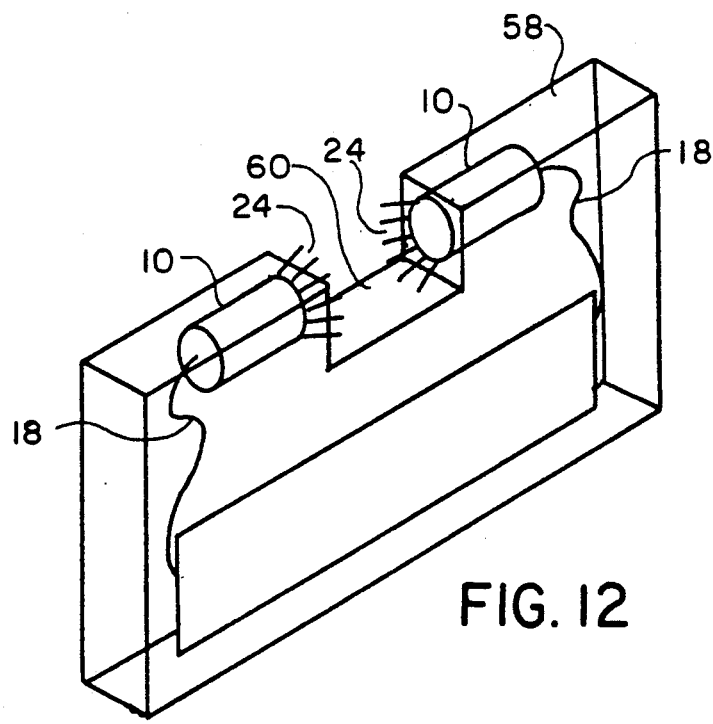
FIG. 12 is yet another form of the invention, using two antennas in a fashion similar to FIG. 10, but with the antennas encased in a unit with a treatment area between the antennas.

FIG. 12 illustrates a form of the invention similar to that shown in FIG. 10, but with a pair of antennas 10 encapsulated within a dielectrically shielded case 58. The antennas 10 are situated at opposite sides of a gap 60 forming a treatment area within the case 58. Each of the antennas 10 is connected by its conductor 18 to a high voltage, high frequency power source 62, described in greater detail in relation to FIG. 18. The source 62 may be encapsulated within the case 58, thus forming a unitary treatment device, or may be separate from the case 58.

As explained above, the power source provides a high frequency, high voltage output. A preferred wave form is shown in FIG. 13. As shown, the wave form illustrated in FIG. 13 is a damped spiked sinusoidal wave which is pulsed at a frequency of 120 Hz. The frequency of the wave is preferably on the order of ½ MHz.

The corona output from each of the antennas 10—10'''' is schematically illustrated in FIG. 14. The antenna output is a broad band high frequency output with random frequencies ranging from 0 Hz to more than 1 GHz. The entire spectrum between the outer limits of the output is randomly and regularly represented in the output spectrum of each antenna.

Figure 15:
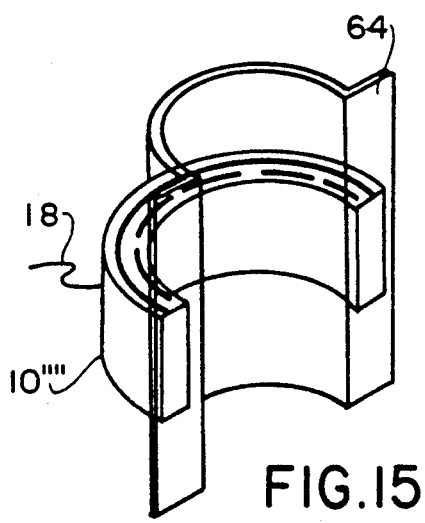
FIG. 15 illustrates dielectric shielding in combination with the form of the invention shown in FIG. 9.
Figure 17:
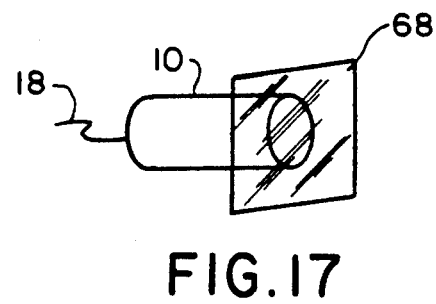
FIG. 17 illustrates a different form of dielectric shielding that may be employed with all forms of the invention.
Figure 16:
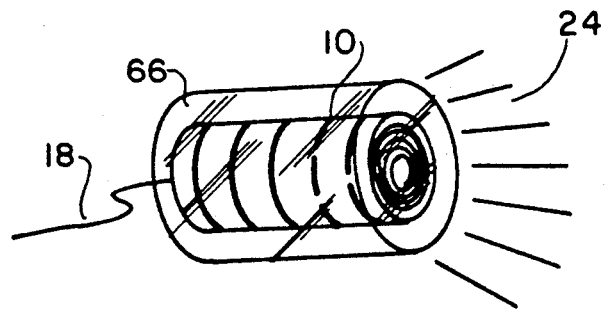
FIG. 16 illustrates dielectric shielding in combination with the form of the invention shown in FIGS. 2-4.

FIGS. 15-17 illustrate various forms of dielectric shielding for the various antennas 10—10''''. In FIG. 15, a low loss plastic dielectric plate shield 64 is shaped to engage the antenna 10''''. The shield 64 extends sufficiently beyond the antenna 10'''' to prevent any arcing around edges of the sheet 64.

In FIG. 16, an antenna 10 is shown encased within a low loss dielectric shield 66. In FIG. 17, a plate shield 68 is employed, rather than fully encapsulating the antenna 10. In all instances, the shields 64-68 are low loss plastic dielectric shielding which insulate against arcing when treating a musculoskeletal disorder, but which permit the high frequency electrostatic corona discharge to contact the treatment area. Where the antenna is not enveloped within a shield, the size of the shield is sufficient to prevent arcing around the edges of the shield.

A high voltage power source, such as the power source 62, is illustrated in FIG. 18. The source in FIG. 18 is intended for driving a pair of antennas 10—10'''', while that of FIG. 19, described below, is for driving a single antenna.

The power source 62 includes a source of line voltage 70 connected to a transformer 72 through a resistor 74 and a variable resistor 76. A power switch 78 is used to connect power to the transformer 72.

The transformer 72 steps up the voltage from the source 70, and is connected to a pair of chokes 80 and 82. A spark gap 84, used for generating the low frequency pulsing of the power source 62, bridges between the chokes 80 and 82. Voltage pulses are passed through capacitors 86 and 88 to primaries 90 and 92 coupled to secondary coils 94 and 96 connected to respective conductors 18 of the two antennas 10.

Figure 19:
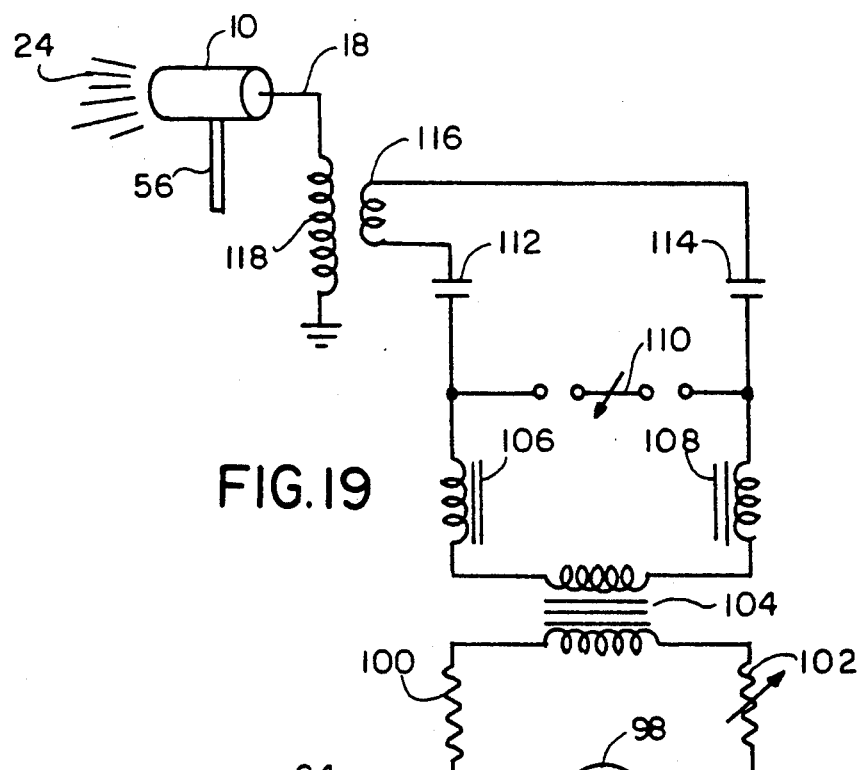
FIG. 19 is a schematic circuit illustration for providing power to a single antenna according to the invention.

The single antenna power source is illustrated in FIG. 19. Again included is a line voltage source 98 connected through a resistor 100 and variable resistor 102 to a transformer 104. Radio frequency chokes 106 and 108 lead from the transformer 104 to a spark gap 110, with voltage pulses then proceeding through a pair of capacitors 112 and 114 to a primary coil 116 coupled to a secondary coil 118 connected to the conductor 18 leading to antenna 10.

Other circuits may be devised, as well, to provide the high voltage, high frequency power output required for operating the antennas 10—10'''', although those illustrated in FIGS. 18 and 19 are quite adequate. For purposes of understanding of the circuits of FIGS. 18 and 19, a following table of types and values of the various circuit elements is provided:

| Table of Components | | |
|---|---|---|
| Resistors | 74, 100 | 100 ohm |
| Resistors | 76, 102 | 300 ohm rheostat |
| Transformers | 72, 104 | 5 KV |
| RF Chokes | 80, 82, 106, 108 | 5 mH |
| Spark gaps | 84, 110 | rotary or fixed-variable type |
| Capacitors | 86, 88 | 0.006 μF |
| Capacitors | 112, 114 | 0.005 μF |
| Primaries | 90, 92 | 15 μH |
| Primary | 116 | 20 μH |
| Secondaries | 94, 96 | 5 mH high voltage coil |
| Secondary | 118 | 5 mH high voltage coil |

While the power sources of FIGS. 18 and 19 are preferred forms of suitable power sources, other power sources might be employed as well, so long as they meet the criteria of the present application, that being a high voltage source on the order of 100,000 to 200,000 volts, a high frequency on the order of ½ MHz, and a total power output of between 5 to 15 watts, producing a broad band high frequency random output from the antenna with frequency varying from 0 Hz to more than 1 GHz.

The strips 12 and 42 are excited by the high voltage applied, and produce a corona discharge through the interior and exterior of the antennas 10—10'''. It is preferred that the strips 12 and 42 have relatively sharp edges which promote high voltage corona discharge among the adjacent strips. The strips are arranged on the sheets 14 and 44 in such a way as to promote random arcing. While the elongated, thin conductive strips illustrated in the drawings are preferred, strips of any size or shape may be employed, depending on the corona output desired from the antenna. The capacitance of an antenna and ability to hold an electrostatic charge increases as the size and number of the strips 12 or 42 increases.

While the antennas 10—10'''' have been shown as either fixed or handheld for applying corona to a body, they may be otherwise held in registration to a treatment area, such as by retaining straps. How the antennas are situated relative to the body will necessarily depend upon the area to be treated.

In use, the invention is employed with an antenna 10—10'''' held directly against the body or within about ½ inch of the area to be treated. The duration of exposure to the corona depends upon the area to be treated, and can vary from 30 seconds to 30 minutes or more. Because internal heating is not an essential feature of the present invention, there is little or no danger of overtreatment, and little or no effect on normal tissue. Depending on the treatment and disorder to be treated, the invention produces salutary effects, such as (1) long-lasting reduction or elimination of pain and soreness associated with arthritis and other inflammatory diseases, (2) increased blood circulation in the treated area, (3) increased mobility of a treated joint or area, and (4) decreased swelling of the inflamed joint or treated area. While, just after treatment, some areas may respond with an increase in swelling, this is the body's response to the healing process, and swelling decreases very shortly after treatment.

Various changes can be made to the invention without departing from the spirit thereof or scope of the following claims.

What is claimed is:

1. An electrotherapy device for treatment of musculoskeletal disorders, comprising
   a. an antenna having a voltage application location and a corona discharge location, said locations being spaced from one another, said antenna comprising
      i. a plurality of spaced rows of conductive strips between said application location and said discharge location, each row having at least one strip with the number of strips in each row increasing generally from said application location to said discharge location, and
      ii. means mounting said rows of strips,
   b. a high voltage, high frequency, low power source connected to said application location, and
   c. dielectric shielding means at said discharge location for preventing arcing from said device during treatment of a disorder.

2. An electrotherapy device according to claim 1 in which said mounting means comprises a flexible dielectric plastic sheet, said strips being secured to said sheet.

3. An electrotherapy device according to claim 2 in which said strips are secured in parallel rows to said sheet, and in which said sheet is wound into a spiral coil, with said application and discharge locations being situated at opposite ends of said coil.

4. An electrotherapy device according to claim 3 in which said dielectric shielding means encases said coil.

5. An electrotherapy device according to claim 2 in which said strips are secured in parallel rows to said sheet, and in which said sheet is wound into spaced, spiral convolutions.

6. An electrotherapy device according to claim 5 including a series of pegs spacing each said convolution from the next convolution.

7. An electrotherapy device according to claim 2 in which said strips are secured in parallel rows to said sheet, and in which said sheet is formed into an accordion folded stack with said discharge and application locations being on opposite sides of said stack.

8. An electrotherapy device according to claim 7 in which said dielectric shielding means comprises a low loss dielectric plastic plate at said discharge side of said stack.

9. An electrotherapy device according to claim 2 in which said strips are secured to said sheet in curved, radially spaced rows, said discharge location being located in a treatment area at least partially enveloped by an inner row.

10. An electrotherapy device according to claim 9 including a stacked and aligned plurality of said sheets.

11. An electrotherapy device according to claim 10 in which said shielding means comprises a formed plastic shield conforming to said treatment area.

12. An electrotherapy device according to claim 1 in which said dielectric shielding means comprises a low loss dielectric plate located at said corona discharge location.

13. An electrotherapy device according to claim 1 including a pair of said antennas spaced from one another with a treatment area being located between the corona discharge locations of said antennas.

14. An electrotherapy process for treatment of musculoskeletal disorders, comprising the steps of
   a. forming an antenna having a series of spaced conductive strips of varying lengths, said strips being oriented laterally between a voltage application location and a corona discharge location,
   b. generating a high voltage, high frequency source, said source being pulsed at a low frequency rate, to produce a broadband output corona discharge from said discharge location having an electrostatic field extending in frequency from 0 Hz to over 1 GHz and constantly changing randomly in amplitude and frequency,
   c. applying said source to said application location and to only one of said strips to produce said corona discharge, and
   d. directing said corona discharge to a surface of a body in a region experiencing a musculoskeletal disorder.

15. An electrotherapy process according to claim 14 in which said high voltage is in the range of from about 100,000 to about 200,000 volts.

16. An electrotherapy process according to claim 15 in which said high voltage is about 150,000 volts.

17. An electrotherapy process according to claim 14 in which said high frequency is about ½ MHz.

18. An electrotherapy process according to claim 14 in which low frequency rate is about 120 Hz.

19. An electrotherapy process according to claim 14 in which said source has a power output of from 5-15 watts.

20. An electrotherapy process according to claim 19 in which said power output is about 10 watts.

* * * * *